United States Patent [19]

Stevenson et al.

[11] Patent Number: 4,928,682

[45] Date of Patent: May 29, 1990

[54] AIRCRAFT ON-BOARD OXYGEN GENERATING SYSTEMS

[75] Inventors: George F. Stevenson; James C. Foote; Humphrey A. S. Hamlin, all of Somerset, England

[73] Assignee: Normalair-Garrett (Holdings) Limited, United Kingdom

[21] Appl. No.: 252,141

[22] Filed: Oct. 3, 1988

[30] Foreign Application Priority Data

Oct. 14, 1987 [GB] United Kingdom ................. 8724081

[51] Int. Cl.⁵ ............................................ A61M 15/00

[52] U.S. Cl. ........................... 128/202.26; 128/205.24

[58] Field of Search ....................... 128/202.26, 205.11, 128/205.24, 204.25

[56] References Cited

U.S. PATENT DOCUMENTS

| | | | |
|---|---|---|---|
| 2,378,468 | 6/1945 | Deming | 128/205.11 |
| 2,403,508 | 7/1946 | Deming | 128/205.11 |
| 2,767,727 | 10/1956 | Acomb | 128/204.25 |
| 2,818,860 | 1/1958 | Holm et al. | 128/204.25 |
| 3,386,458 | 6/1968 | Wasserman et al. | 128/205.11 |
| 3,441,041 | 4/1969 | Schreiber | 128/204.25 |
| 3,788,311 | 1/1974 | Fahlmar et al. | 128/205.11 |
| 3,875,957 | 4/1975 | Veit et al. | 128/205.11 |
| 3,952,773 | 4/1976 | Hahn | 128/204.25 |
| 4,066,076 | 1/1978 | Williamson | 128/204.25 |
| 4,428,372 | 1/1984 | Beysel et al. | 128/202.26 |

*Primary Examiner*—Edgar S. Burr
*Assistant Examiner*—Aaron J. Lewis
*Attorney, Agent, or Firm*—Larson and Taylor

[57] ABSTRACT

An on-board oxygen generating system (OBOGS) includes a molecular sieve oxygen generating system (MSOGS), a breathable gas delivery regulator selectively operable to deliver 100 percent MSOGS output gas or air diluted output gas to a user, a back-up storage plenum and control means arranged so that when air diluted delivery gas is selected a portion of 100 percent MSOG output gas is diverted to charge the storage plenum and when 100 percent MSOG output delivery gas is selected diversion to the storage plenum is automatically prevented. The breathable gas delivery regulator includes an injector adapted to induce a flow of air to mix with 100 percent MSOG output gas when air diluted delivery gas is selected.

11 Claims, 3 Drawing Sheets

AIRCRAFT ON-BOARD OXYGEN GENERATING SYSTEMS

BACKGROUND OF THE INVENTION

1. Field of the Invention

This invention relates to aircraft on-board oxygen generating systems (OBOGS) and to breathable gas delivery regulators of the demand type for use therein.

An OBOGS derives oxygen from the ambient air by passing the air through a molecular sieve oxygen generator system (MSOGS) which delivers breathable gas having a high oxygen concentration for supply through a regulator to a user.

2. Description of the Prior Art

U.S. Pat. No. 4428372 discloses an OBOGS in which a proportion of the breathable gas is also used to charge, through a control valve, an emergency storage tank to dispense with the requirement for the oxygen bottles or liquid store of prior systems. The control valve is controlled by an oxygen partial pressure sensor which allows charging of the emergency tank when the oxygen concentration is between 60 and 95 per cent.

This wide range of oxygen concentration of the stored gas is undesirable firstly, because a user is never certain of the actual concentration of the stored gas at any particular time and secondly because, certainly at the lower end of the range, the concentration would be inadequate for use at high cabin altitudes. Consequently it is desirable that an emergency or back-up breathing gas supply has a concentration of oxygen that is adequate to cater for the worst operational case and should therefore be at least 90 per cent, and which can be guaranteed to be maintained at that level.

There is now also a requirement in the art for a supply of oxygen-enriched breathable gas to be available whilst the aircraft is on the ground either with or without its engines running. Certainly in the latter case the breathable gas has to be drawn from an on-board storage tank and, since in such a case the contents of the storage tank could become significantly depleted, it is essential that recharging is completed as quickly as possible.

The prior art device may not be suitable for such installations firstly because as hereinbefore mentioned the oxygen concentration of the stored gas may not be adequate and, secondly, the charging and control system disclosed in the prior art system may result in an undesirable delay in replenishment of the emergency storage tank.

SUMMARY OF THE INVENTION

Accordingly, in one aspect, this invention provides an aircraft on-board oxygen generating system (OBOGS) in which oxygen-enriched breathable gas is derived from a molecular sieve oxygen generating system (MSOGS) for supply through a breathable gas delivery regulator having a first operating position in which 100 per cent MSOGS output gas is delivered to a user and a second operating position in which air diluted output gas is delivered to a user, the OBOGS including a back-up storage plenum for storing breathable gas and control means arranged so that with the regulator positioned to deliver air diluted breathable gas to the user a portion of the 100 per cent MSOG output gas is diverted from upstream of the regulator to charge the storage plenum and with the regulator positioned to deliver 100 per cent MSOGS output gas to the user diversion of the output gas is not permitted.

The control means may include a switch associated with the regulator and controlling an electric supply to an electrically operated charge inhibit valve located in a branch pipe opening into a breathable gas delivery pipe between the MSOGS and the regulator and communicating with the storage plenum. Preferably the control means is arranged to permit flow through the branch pipe into the storage plenum when the charge inhibit valve is energised.

Conveniently, an electrically operated back-up release valve is located in the breathable gas delivery pipe between the MSOGS and the regulator and includes an inlet from the storage plenum whereby the valve provides for a flow of breathable gas to the regulator either from the MSOGS or from the storage plenum. Preferably the valve is arranged so as to permit flow from the MSOGS when energised.

The breathable gas delivery regulator may include a demand valve adapted during operation to supply breathable gas through an outlet passage and a selectively operable breathable gas flow control valve to an outlet duct, a selectively operable air inlet valve for connecting an air supply into said outlet duct and an injector nozzle opening into an upstream end of the outlet duct, wherein when the regulator is to deliver air diluted breathable gas the air inlet valve is opened and the breathable gas flow control valve is closed to direct all of the breathable gas supply through the injector nozzle to induce a flow of air through the air inlet valve into the outlet duct.

Preferably, the breathable gas flow control valve is a pneumatically operated valve spring-loaded to the open position, and may comprise a radially extending valve head formed externally of an axially movable injector nozzle for engagement with a valve seat.

The movable injector nozzle may include a central bore at one end communicating through radial apertures with the outlet passage upstream of the valve head and an outlet nozzle opening axially into the outlet duct. The other end of the movable jet nozzle may be supported by a diaphragm located in a chamber and control means may be provided for pressurising the chamber when air mix mode is selected so as to close the breathable gas flow control valve.

A mixing tube may be located in the outlet duct concentrically of the jet nozzle outlet.

In an alternative embodiment the breathable gas flow control valve may comprise a valve head at one end of an axially movable valve for engagement with a valve seat located between the demand valve outlet passage and an annulus at one end and in communication with the outlet duct. Conveniently, the other end of the valve may be supported by a diaphragm located in a chamber and control means may be provided for pressurising the chamber when air-mix mode is selected to close the breathable gas flow control valve.

In this embodiment the injector nozzle may comprise a fixed nozzle having a central passageway opening into the outlet passage upstream of the valve head and an outlet nozzle opening axially into the upstream end of the outlet duct centrally of the annulus. Conveniently, the upstream end of the outlet duct may have a venturi shape.

In both embodiments, the air inlet valve may comprise a pneumatically operated valve having a valve head at one end spring loaded into engagement with a valve seat. The other end of the valve may be supported by a diaphragm in a chamber and control means may be provided for pressurising the chamber to open the air inlet valve when air dilution is selected.

In another aspect the invention provides a breathable gas delivery regulator for receiving an oxygen-enriched breathable gas supply and having a first operating position in which undiluted breathable gas is delivered to a user and a second operating position in which air diluted breathable gas is supplied, the regulator including a demand valve adapted during operation to supply breathable gas through an outlet passage and a selectively operable breathable gas flow control valve to an outlet duct, a selectively operable air inlet valve for connecting an air supply into the outlet duct and an injector nozzle opening into a upstream end of the outlet duct, wherein when air dilution is selected the air inlet valve is opened and the breathable gas flow control valve is closed to direct all of the breathable gas flow through the injector nozzle to induce a flow of air through the inlet valve into the outlet duct.

BRIEF DESCRIPTION OF THE DRAWINGS

The invention will now be described by way of example only and with reference to the accompanying drawings in which.

DETAILED DESCRIPTION OF THE DRAWINGS

Figure 1:
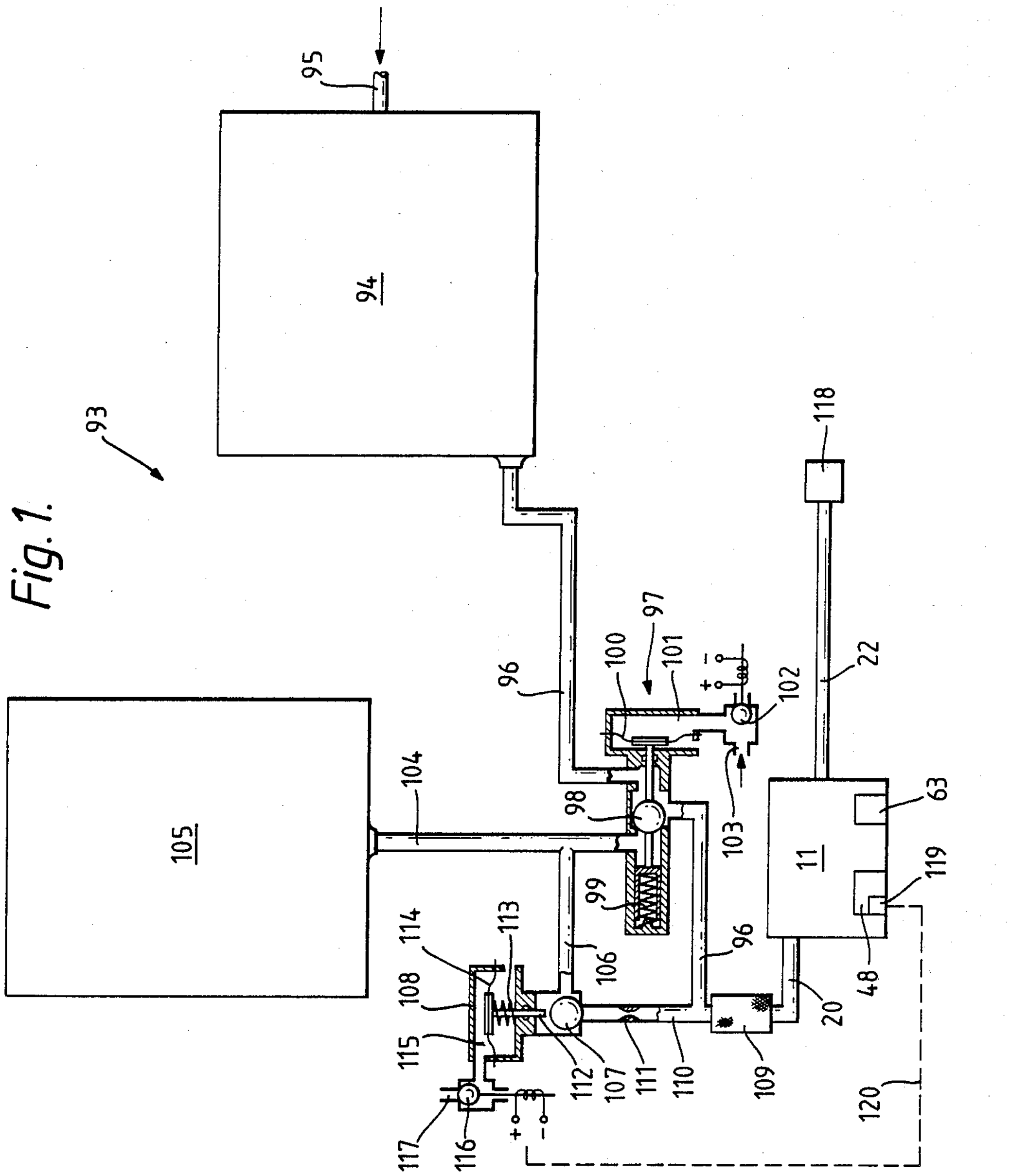
FIG. 1 is a schematic illustration of an aircraft onboard oxygen generating system according to one embodiment of the invention.

Referring now to FIG. 1, an aircraft on-board oxygen generating system (OBOGS) 93 includes a molecular sieve oxygen generator (MSOG) 94 having an inlet 95 connected to a supply of compressed air. A breathable gas delivery pipe 96 connects to the inlet of a back-up release valve 97 having a valve head 98 biased by a spring 99 and operatively associated with a diaphragm 100 located in a chamber 101 which opens through a solenoid controlled valve 102 to an inlet 103 connected to a supply of compressed air. Back-up release valve 97 is shown with solenoid valve energised.

A pipe 104 connects valve 97 to the interior of a back-up breathing gas storage plenum 105 and a branch pipe 106 connects a pipe 104 to one side of a valve head 107 of a charge inhibit valve 108. Delivery pipe 96 connects valve 97 through a filter 109 to an inlet passage 20 of a breathable gas delivery regulator 11 and a branch pipe 110 connects delivery pipe 96 to the other side of valve head 107. Pipe 110 contains a flow restrictor 111.

Charge inhibit valve 108 includes a plunger 112 biased by a spring 113 and supported by a diaphragm 114 located in a chamber 115 which opens through a solenoid controlled valve 116 to an inlet 117 connected to a supply of compressed air. Charge inhibit valve 108 is shown with the solenoid controlled valve 116 energised.

Breathable gas delivery regulator 11 includes an outlet duct 22 connected to a user's mark 118 and a three position mode selector switch 48 which is described in detail hereinafter but which briefly is used to supply either 100 per cent MSOG product gas or air diluted MSOG product gas to the mask 118. Regulator 11 includes an air inlet valve 63 and a switch 119 associated with mode selector switch 48 connected electrically as shown at 120 with the solenoid valve 116 associated with charge inhibit valve 108. A further switch (not shown) is connected electrically with the solenoid valve 102 associated with back-up release valve 97.

A breathable gas delivery regulator 11 (FIG. 2) includes a pressure balanced demand valve 12 generally of the type disclosed in EP-A-0078644 and comprising an axial piston 13 having labyrinth grooves 14 in its external surface. The piston 13 is joined by a reduced diameter stem 15 to a valve head 16 associated with a valve seat 17 which separates an inlet chamber 18 from an outlet chamber 19, the former being connected via an inlet passage 20 to a breathable gas supply and the latter through an outlet passage 21 to an outlet duct 22. Valve head 16 is biased towards seat 17 by a spring 23.

The end of piston 13 contacts a pivoted lever 24 which extends into a demand pressure sensing chamber 25 for contact by a plate 26 supported by a sensing diaphragm 27 which separates chamber 25 from a cabin pressure sensing chamber 28. Sensing diaphragm 27 is biased by a spring 29 in chamber 28.

Chamber 25 is pneumatically connected through passage 30 into outlet duct 22 and chamber 28 is pneumatically connected through passage 31 to a chamber 32 of a spring-loaded compensated dump valve 90.

A lower flanged end 33 of a safety pressure control valve 34 is slidably located through an upper support plate 35 supported by the diaphragm 27. Valve 34 extends into a chamber 36 where its upper end is supported by a diaphragm 37 biased by a spring 38.

Inlet passage 20 is pneumatically connected through passage 39 to valve seats 40 and 41 opening into chambers 42 and 43. The chambers 42 and 43 contain spring-loaded valves 44 and 45 for selective co-operation with the valve seats 40 and 41, the valves 44 and 45 protruding from the regulator 11 for co-operation with interconnected cam plates 46 and 47 of a three position mode selector switch 48. Chamber 43 is pneumatically connected through outlet passage 49 with safety pressure control chamber 36 and chamber 42 is pneumatically connected through outlet passage 50 to an injector nozzle control chamber 51 and an air inlet valve control chamber 52.

Switch 119 (see also FIG. 1) is operated by a spring-loaded plunger 121 contacting cam plate 47 which includes a recess 122 for engagement by the plunger as hereinafter described.

Control chamber 51 is bounded in part by a flexible diaphragm 53 which supports centrally one end of an injector nozzle 54 having an outer nozzle end 55 protruding centrally into outlet duct 22. Nozzle end 55 is fed by a central bore 56 communicating through radial apertures 57 with outlet passage 21 upstream of a breathable gas flow control valve or injector nozzle by-pass means by-pass means including injector nozzle by-pass control means comprising a radially extending valve head 58 arranged for co-operation during certain phases of operation with a valve seat 59 that provides communication between outlet passage 21 and outlet duct 22. Nozzle 55 is aligned centrally with the inlet of a mixing tube 60 located centrally of outlet duct 22. Valve head 58 is biased away from valve seat 59 by a spring 61.

Control chamber 52 is bounded in part by a flexible diaphragm 62 which supports centrally one end of an air inlet control valve 63 having a valve head 64 normally biased by spring 65 into contact with a valve seat 66 which connects with an air inlet. Valve seat 66 communicates through a chamber 67 containing an air mix control aneroid capsule 68 and associated seat 69 and an air inlet check valve 70 with the interior of outlet duct 22 adjacent the inlet end of mixing tube 60.

A passage 92 connects the demand valve cylinder downstream of the labyrinth grooves 14 on piston 13 with chamber 28 and a maximum pressure relief valve 71, and through a branch passage 72 with a chamber 73 containing a pressure breathing aneroid capsule 74. Outlet passage 75 connects chamber 73 through a mask test relief valve 76 and a mask test switch 77 to ambient.

Figure 2:
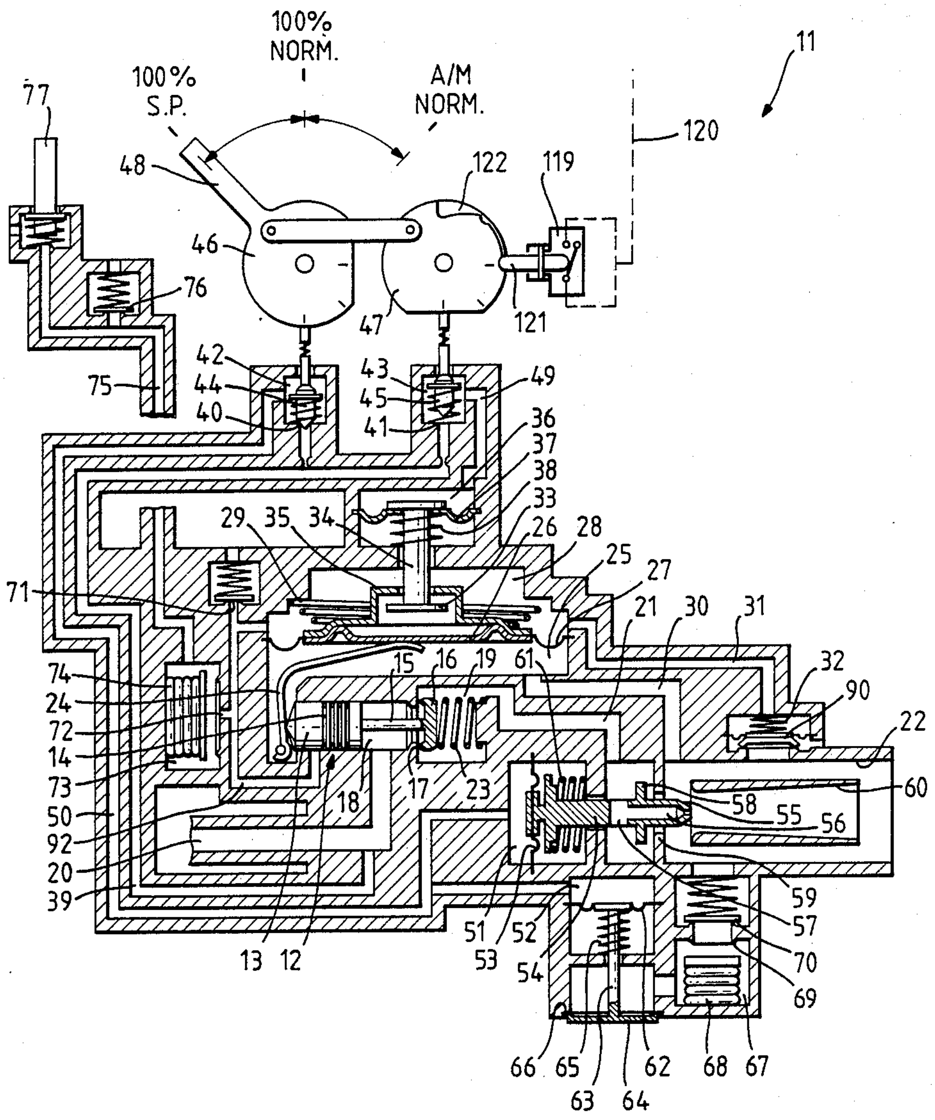
FIG. 2 is a sectioned view of one type of breathable gas delivery regulator suitable for use in the system of FIG. 1.
Figure 3:
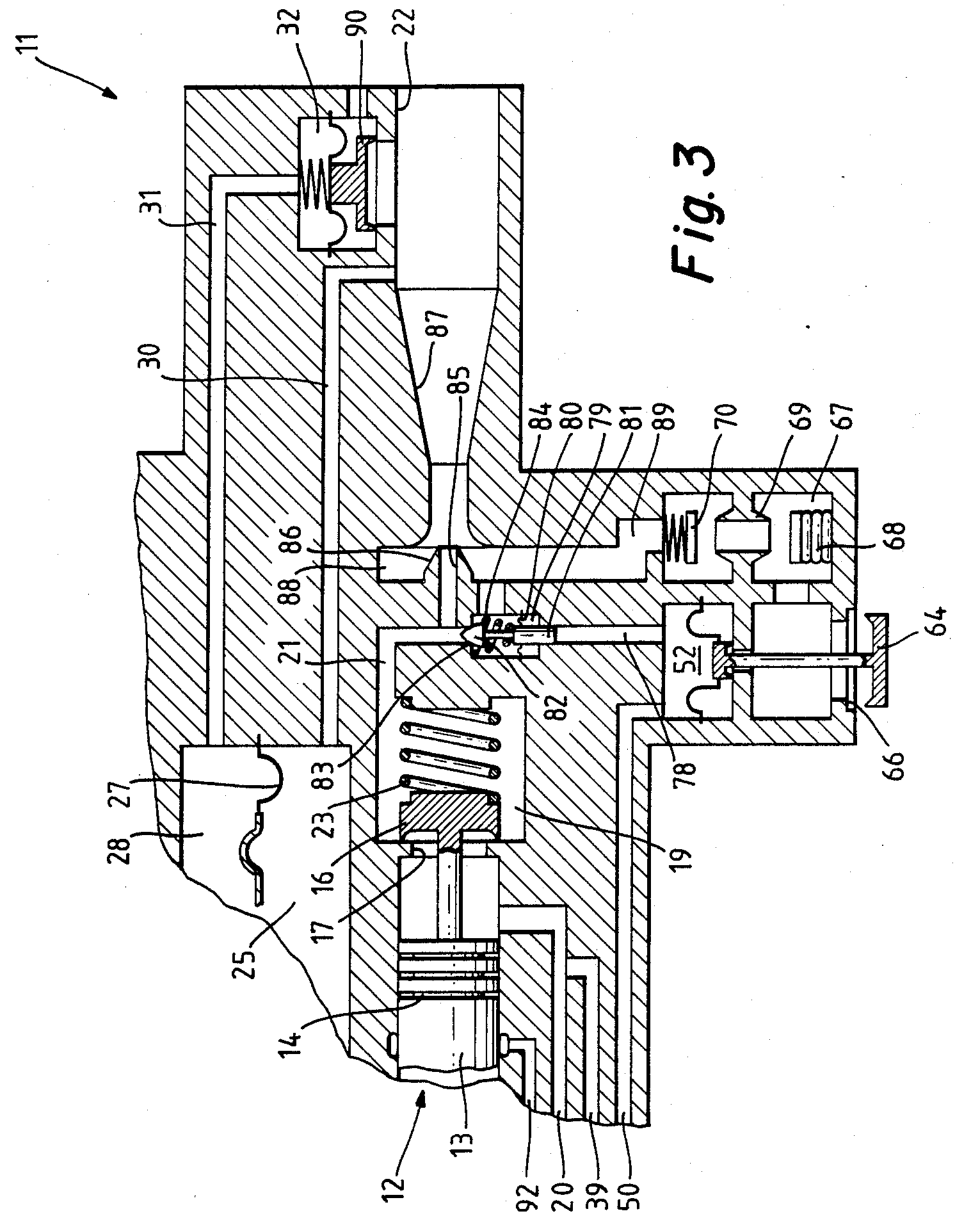
FIG. 3 is a fragmentary sectioned view of another type of breathable gas delivery regulator suitable for use in the system of FIG. 1.

In the embodiment of FIG. 3, like reference numerals have been used to indicate parts similar to that previously described in relation to FIG. 2, and the following description will concentrate on the areas of difference only.

Branch passage 78 connects chamber 52 with a chamber 79 bounded by a diaphragm 80 supporting a slidable breathable gas flow control valve 81 having a valve head 82 for co-operation during certain phases of operation with a valve seat 83. Valve 81 is biased by a compression spring 84 to a position in which the valve head 82 is normally retained off the seat 83. Seat 83 is located between outlet passage 21 and an annulus 88 opening into a venturi-shaped upstream end 87 of outlet duct 22, and a branch passage 85 opens into passage 21 upstream of valve 81 and comprises the central bore of a fixed injector nozzle 86. Nozzle 86 opens centrally into the venturi-shaped upstream end 87 of outlet duct 22 and annulus 88 is pneumatically connected downstream of seat 83 and via passage 89 to pressure relief valve 70, chamber 67 and valve seat 66 to ambient.

In operation of the OBOGS 93 of FIG. 1, compressed air enters the MSOG 94 through inlet 95 and oxygen-enriched bas (typically 90–95 per cent concentration) is delivered in a known manner into delivery pipe 96 to back-up release valve 97.

With solenoid valve 102 energised (i.e. in the position shown in FIG. 1) chamber 101 is pressurised with compressed air to position the diaphragm 100 and associated valve 98 to allow a flow of breathable gas through valve 97, filter 109 and inlet passage 20 to breathable gas delivery regulator 11 and thence through outlet duct 22 to mask 118.

If the pressure in storage plenum 105 is low, and provided that the solenoid valve 116 controlling charge inhibit valve 108 is energised as illustrated in FIG. 1, then chamber 115 is vented to atmosphere and some of the breathable gas can flow through branch pipe 110, restrictor 111, valve 107 and pipes 106 and 104 to recharge the plenum 105. Preferably, the storage plenum 105 is filled with an oxygen adsorbing material to ensure maximum concentration of stored gas for a minimum size and weight of plenum.

It will be apparent that the operation of switch 119 to de-energise solenoid valve 116 admits pressurised air through inlet 117 into chamber 115 to move diaphragm 114 and the associated plunger 112 against spring 113 to retain valve 107 against a seat opening into pipe 110 to prevent breathable gas entering plenum 105. Similarly, when the switch (not shown) is operated to de-energise solenoid 102, chamber 101 is vented to atmosphere and valve 98 of back-up release valve 97 is moved by spring 99 to shut off the flow of breathable gas through pipe 96 and to connect the back-up supply in plenum 105 through pipe 104 filter 109 and inlet passage 20 to regulator 11 for supply as required to mask 118.

Operation of the breathable gas regulator 11 and in particular pressure balanced demand valve 12 is similar to that disclosed in EP-A-0078644 and is controlled by the inhalatory and exhalatory phases of a user aviator's breathing cycle by way of movement of sensing diaphragm 27 due to corresponding changes in breathing cycle pressure in outlet tube 22 which is effective in chamber 25 through passage 30. Thus, during inhalation, the sensing diaphragm 27 is drawn downwardly to deflect lever 24 which in turn moves valve 12 to the right as viewed in the drawing to move valve head 16 away from seat 17 to feed breathable gas into outlet passage 21 and through the valve seat 59 of the breathable gas flow control valve into outlet duct 22. Conversely, during exhalation a subsequent pressure build up in chamber 25 moves the sensing diaphragm 27 upwardly so that the valve head 16 of demand valve 12 is moved towards the valve seat 17 under the influence of spring 23.

The three positions of mode selector switch 48 are marked respectively 100% S.P. (i.e. 100 per cent MSOGS gas with safety pressure), 100% NORM (i.e. 100 per cent MSOGS gas with normal breathing pressure) and A/M NORM (i.e. air mix with normal breathing pressure). The use of the term 100 per cent in respect of MSOGS output gas does not mean that the gas consists of pure oxygen but that it is undiluted gas as supplied from MSOGS (typically about 90 to 95 per cent oxygen).

FIG. 2 illustrates the regulator 11 in the 100% S.P. condition in which the cam members 46 and 47 operate to close valve 44 onto its seat 40 and to allow valve 45 to move away from seat 41 under the influence of the spring.

Thus, inlet gas from inlet passage 20 passes through passage 39, valve seat 41 and passage 49 into safety pressure control chamber 36 moving safety pressure control valve 34 downwardly to move flanged end 33 away from the adjacent surface of support plate 35. Sensing diaphragm 27 is free to move downwardly under the influence of spring 29 which biases demand valve 12 towards an open position to provide a low positive safety pressure of breathing gas in outlet duct 22 until the safety pressure (typically 1.5in. WG) forces diaphragm 27 upwardly against the loading of spring 29.

Selection of the 100% NORM position of mode selector 49 serves to close valve 45 whilst retaining valve 44 closed. The closure of valve 45 releases the pressure in chamber 36 to release the safety pressure control valve 34 which moves under the influence of spring 38 to re-engage the flange portion 33 with upper plate 35, so that demand valve 12 is controlled due to the differential pressures across the sensing diaphragm 27 between the cabin pressure in chamber 28 and the demand pressure in chamber 25.

It will be noted that in both of the operative positions 100% S.P. and 100% NORM the injector nozzle 54 is retained under the influence of the spring 61 with the valve head 58 off its seat 59 to allow full flow capacity of breathable gas from outlet passage 21 into outlet duct 22. This allows a sufficient flow of 100 per cent MSOG breathable gas to be obtained by a user which would not be possible through the injector nozzle 54.

Furthermore in both of these positions, plunger 121 is retained by cam plate 47 to break the electrical circuit through switch 119 to de-energise solenoid 116 of back-up release valve 108 (FIG. 1) to prevent breathable gas flowing into plenum 105.

On selection of A/M NORM valve 44 is moved to its open position and valve 45 remains closed. Inlet gas pressure therefore flows through valve seat 40, chamber 42 and passage 50 into chambers 51 and 52. Increasing pressure in chamber 52 operates valve 63 to move valve head 64 away from valve seat 66, and increasing pressure in chamber 51 moves the injector nozzle 54 against spring 61 until valve head 58 contacts valve seat 59. In this condition the full flow of breathable gas from demand valve 12 passes through apertures 57 and central bore 56 to exhaust through nozzle end 55 into the centre of mixing tube 60 which induces a flow of air through valve seat 66, chamber 67 and check valve 70 to mix with the MSOGS output gas at the upstream end of outlet duct 22.

With increasing cabin altitude, air mix control aneroid capsule 68 and pressure breathing aneroid capsule 74 expand. Expansion of the former restricts the flow of air through seat 69 to regulate the ratio of air to MSOGS gas to maintain the required oxygen partial pressure of the breathable gas with cabin altitude.

Expansion of aneroid capsule 74 restricts flow through passage 72 resulting in an increase in pressure in chamber 28 which in turn further deflects the diaphragm downwardly with a subsequent increase in the pressure of breathable gas in the outlet duct 22.

The compensated dump valve 90 ensures that pressure in outlet duct 22 will relieve, should the pressure exceed that in chamber 28 by more than a predetermined amount, and pressure relief valve 71 will relieve when the pressure in chamber 28 reaches a predetermined maximum pressure that is set by the maximum altitude at which the regulator 11 is designed to operate.

Mask test switch 77 provides a manual test facility for checking that a breathing mask attached to outlet duct 22 is fitting correctly and that there are no appreciable leaks in the breathable gas delivery system. Closing mask test switch 77 results in a build up of pressure in chamber 28 with consequent opening of demand valve 12 to provide breathable gas in outlet duct 22. Excess pressure in chamber 28 is relieved through mask test relief valve 76.

When mode selector switch 48 is in the A/M NORM position recess 122 is aligned with plunger 121 which enters the recess to make the electrical circuit through switch 119 to energise the solenoid 116 of valve 108 (FIG. 1) and permit breathable gas to enter plenum 105 as hereinbefore described.

The regulator of FIG. 3 operates in the 100% S.P. and 100% NORM positions identically to that previously described with reference to the embodiment of FIG. 2. In those positions, valve head 82 is retained away from seat 83 so that breathable gas in outlet passage 21 flows into annulus 88 and thence into outlet duct 22.

FIG. 3 shows the valve in the A/M NORM position in which breathable gas is fed through passage 51 into chamber 52 to move valve head 64 away from seat 66. In this embodiment the gas flows also through passage 78 into chamber 79 and acts on diaphragm 80 to overcome the spring and move valve head 82 of breathable gas flow control valve 81 into engagement with seat 83. Thus, all of the flow of breathable gas from demand valve 12 passes through the central bore 85 of fixed jet nozzle 86 into the venturi 87 which induces a flow of air through valve seat 66 to mix with the MSOGS output gas at the upstream end of outlet duct 22.

The incorporation of the air dilution facility in the OBOGS of this invention significantly reduces the flow of breathable gas that is required to be drawn from the MSOGS and ensures that the product gas from the MSOGS has a high oxygen concentration i.e. at least 90 per cent all the time that A/M NORM mode is selected. The invention recognises that the oxygen concentration in the 100% NORM and 100% SP modes may fall below 90 per cent and therefore incorporates a control system which ensures that recharging of storage plenum 105 occurs only when A/M NORM is selected. Since this is the mode that is used during the majority of any normal flight the plenum 105 is always recharged as quickly as possible and with gas having an adequately high oxygen concentration. The control system incorporates selectively operable means to enable a user to draw breathable gas from the plenum not only in an emergency but also when the aircraft is on the ground or in high risk conditions e.g. during take-off, and again ensures that the oxygen concentration is at the required high level.

In the event that a crew member selects back-up, or automatically in the event of an electrical failure or an indicated failure of the MSOG 94, the solenoid 102 of back-up release valve 97 is de-energised to isolate the MSOG 94 and allow breathing gas to flow from the plenum 105 to mask 119. Means are provided (not shown) to ensure that when plenum 105 becomes exhausted, the back-up release valve is automatically re-energised to allow breathing gas to be obtained from the MSOG.

The OBOGS incorporates a breathable gas delivery regulator of the type disclosed in EP-A-0078644 thereby ensuring efficient operation at the low MSOG output pressures, and the incorporation of the pneumatically operated jet nozzle ensures efficient air entrainment into the outlet duct without the need to incorporate a compressor device to increase the pressure of the MSOG outlet gas.

The selectively operable combination in the regulator of the injector nozzle and the breathable gas flow control valve ensures efficient operation in all modes. Thus, the directing of the entire flow of breathable gas through the injector nozzle in the air mix mode ensures that sufficient energy is imparted to the flow for efficient air entrainment, and the automatic opening of the breathable gas flow control valve in other modes ensures that a sufficient flow of breathable gas enters the outlet duct to meet the requirements of higher demanded flows with no entrained air. Furthermore, the arrangement minimises undesirable oscillatory activity of the outlet gas pressure which could result due to pressure build-up behind the nozzle in a regulator in which excess pressure was relieved by a spring-loaded or flexible nozzle type relieving injector or spring-loaded by-pass relief valves.

Whilst several embodiments have been described as illustrated, it will be understood that many modifications may be made without departing from the scope of the invention. For example, control valves 44 and 45 may comprise electrically operated, remotely controlled solenoid valves. A barometric control means may be incorporated in addition to solenoid 102 to release the pressure in chamber 101 of back-up release valve 97 to automatically switch to back-up supply in the event of a sudden decompression. In some installations it may be desirable to incorporate a gas compressor to increase the pressure of the gas stored in the storage plenum 105, which would require a pressure reducer in the outlet, and also an oxygen partial pressure sensor as an additional control of the oxygen concentration of the gas entering the storage plenum. Furthermore, the breathable gas delivery regulator described herein is not limited to use in an OBOGS which is required also to charge a back-up storage plenum but can be used in other OBOGS in which an air dilution facility is desired, e.g. In which a user is not to be supplied with 100 per cent MSOG output gas throughout all operational conditions.

What is claimed is:

1. An on-board oxygen generating system including an aircraft aircrew breathing demand regulator comprising inlet means for receiving a supply of oxygen-enriched breathable gas from a molecular sieve oxygen generating system (MSOGS), outlet means for delivering breathable gas to an end user, demand valve means connected between said inlet means and said outlet means for controlling delivery of MSOGS oxygen-enriched breathable gas from said inlet means to said outlet means in response to breathing demands of the end user, injector means including an injector nozzle connected between said demand valve means and said outlet means and operable by said MSOGS oxygen-enriched breathable gas, injector nozzle bypass means including control means for controlling flow of MSOGS oxygen-enriched breathable gas to bypass said injector nozzle or to be entirely through said injector nozzle in passing from said demand valve means to said outlet means, ambient air inlet means including ambient air inlet control valve means for permitting ambient air to be drawn into said regulator by said injector means, and regulator mode selector switch means for controlling said injector nozzle bypass control means and said ambient air inlet control valve means, whereby in one mode of regulator operation said ambient air inlet control valve means is closed and said injector nozzle bypass means is open to permit undiluted MSOGS oxygen-enriched breathable gas to be delivered to said outlet means and in another mode of regulator operation said ambient air inlet control valve means is open and said injector nozzle bypass means is closed so that MSOGS oxygen-enriched breathable gas flows through said injector nozzle to induce ambient air to enter said regulator to mix with MSOGS oxygen-enriched breathable gas and breathable gas of diluted oxygen concentration is delivered to said outlet means.

2. The system of claim 1, wherein the injector nozzle bypass control means is a pneumatically operated valve spring-loaded to the open position and includes a radially extending valve head formed externally of an axially movable injector nozzle for engagement with a valve seat.

3. The system of claim 2, wherein the movable injector nozzle includes a central bore at one end communicating through radial apertures with the outlet passage upstream of the valve head and an outlet nozzle opening axially into the outlet duct.

4. The system of claim 3, wherein the other end of the movable injector nozzle is supported by a diaphragm located in a chamber, control means being provided for pressurising the chamber when air mix mode is selected so as to close the injector nozzle bypass means.

5. The system of claim 4 including a mixing tube located in the outlet duct concentrically of the jet nozzle outlet.

6. The system of claim 1, wherein the injector nozzle bypass control means comprises a valve head at one end of an axially movable valve for engagement with a valve seat located between the demand valve outlet passage and an annulus at one end and in communication with the outlet duct.

7. The system of claim 6 wherein the other end of the valve is supported by a diaphragm located in a chamber and including control means for pressurising the chamber when air-mix mode is selected so as to close the breathable gas flow control valve.

8. The system of claim 6 wherein the injector nozzle comprises a fixed nozzle having a central passageway opening into the outlet passage upstream of the valve head and having an outlet nozzle opening axially into the upstream end of the outlet duct centrally of the annulus.

9. The system of claim 8 wherein the upstream end of the outlet duct has a venturi shape.

10. An aircraft on-board oxygen generating system comprising a molecular sieve oxygen generating system (MSOGS) adapted for supplying oxygen-enriched breathable gas, a breathable gas delivery regulator connected for receiving undiluted MSOGS breathable gas and for delivering breathable gas to a breathing mask, a mode switch on said regulator for switching said regulator between an airmix mode in which ambient air is permitted to enter the regulator to mix with said MSOGS breathable gas whereby breathable gas of reduced oxygen concentration is delivered by the regulator to the breathing mask and a mode in which undiluted MSOGS breathable gas is delivered to the breathing mask, a back-up storage plenum connected for receiving and storing undiluted MSOGS breathable gas, a back-up storage plenum release valve adapted to control MSOGS breathable gas to be supplied to the regulator from either the MSOGS or the back-up storage plenum as selected by an end user, a back-up storage plenum charge inhibit valve adapted for controlling supply of MSOGS breathable gas to charge said storage plenum, and switch means operable by said mode switch and connected for switching said charge inhibit valve to permit charging of said storage plenum when the mode switch is in a position placing said delivery regulator in an airmix mode of operation and for switching said charge inhibit valve to prevent charging of said storage plenum when the mode switch is in a position placing said delivery regulator in an undiluted MSOGS breathable gas mode of operation.

11. An aircraft on-board oxygen generating system according to claim 10 and further including solenoid means for controlling said back-up storage plenum release valve and said back-up storage plenum charge inhibit valve.

* * * * *